United States Patent
Collaert et al.

(10) Patent No.: US 10,274,452 B2
(45) Date of Patent: Apr. 30, 2019

(54) MICRO-STIMULATION AND DATA ACQUISITION FROM BIOLOGICAL CELLS

(71) Applicants: IMEC, Leuven (BE); Katholieke Universiteit Leuven, K.U. LEUVEN R&D, Leuven (BE)

(72) Inventors: Nadine Collaert, Blanden (BE); Daire J. Cott, Leuven (BE); Michael De Volder, Ghent (BE)

(73) Assignees: IMEC, Leuven (BE); KATHOLIEKE UNIVERSITEIT LEUVEN, K.U. LEUVEN R&D, Leuven (BE)

( * ) Notice: Subject to any disclaimer, the term of this patent is extended or adjusted under 35 U.S.C. 154(b) by 781 days.

(21) Appl. No.: 13/916,308

(22) Filed: Jun. 12, 2013

(65) Prior Publication Data

US 2013/0341185 A1     Dec. 26, 2013

Related U.S. Application Data

(60) Provisional application No. 61/658,822, filed on Jun. 12, 2012.

(51) Int. Cl.
    *G01N 27/327*     (2006.01)
    *B82Y 30/00*      (2011.01)
    (Continued)

(52) U.S. Cl.
    CPC .......... *G01N 27/327* (2013.01); *B82Y 30/00* (2013.01); *G01N 27/308* (2013.01); *G01N 33/4836* (2013.01)

(58) Field of Classification Search
    CPC ................................................... G01N 27/327
    See application file for complete search history.

(56) References Cited

U.S. PATENT DOCUMENTS

| | | | | |
|---|---|---|---|---|
| 4,969,468 A | * | 11/1990 | Byers ............... | A61B 5/0422 29/829 |
| 5,318,572 A | * | 6/1994 | Helland ............ | A61N 1/0565 607/121 |

(Continued)

FOREIGN PATENT DOCUMENTS

WO    WO2009085015 A1    7/2009

OTHER PUBLICATIONS

Miserendino, Scott et al., "Electrochemical Characterization of Parylene-Embedded Carbon Nanotube Nanoelectrode Arrays", Institute of Physics Publishing, Nanotechnology, vol. 17, Jan. 25, 2006, pp. S23-S28.

(Continued)

*Primary Examiner* — Luther Behringer
(74) *Attorney, Agent, or Firm* — McDonnell Boehnen Hulbert & Berghoff LLP

(57) ABSTRACT

The present invention relates to a method for fabricating a semiconductor device for stimulation and/or data recording of biological material to a such semiconductor device. The method comprises providing a semiconductor substrate comprising a first insulating layer; providing a patterned conductive layer on top of the first insulating layer; depositing and patterning a second insulating layer atop the patterned conductive layer; growing carbon nano-sheets atop the second insulating layer; and defining carbon nano-sheet electrode areas on the second insulating layer by etching away the carbon nano-sheets outside of the carbon nano-sheet electrode areas.

16 Claims, 7 Drawing Sheets

(51) Int. Cl.
    *G01N 27/30*    (2006.01)
    *G01N 33/483*   (2006.01)

(56) References Cited

U.S. PATENT DOCUMENTS

| | | | | |
|---|---|---|---|---|
| 7,852,612 | B2* | 12/2010 | Zhao | H01G 11/36 |
| | | | | 252/502 |
| 2002/0009861 | A1* | 1/2002 | Narwankar | C23C 16/56 |
| | | | | 438/404 |
| 2006/0276702 | A1* | 12/2006 | McGinnis | A61B 5/0408 |
| | | | | 600/372 |
| 2008/0232028 | A1 | 9/2008 | Zhao | |
| 2011/0172736 | A1* | 7/2011 | Gefen | A61N 1/0543 |
| | | | | 607/54 |

OTHER PUBLICATIONS

Chen, Xu et al., "A high performance electrochemical sensor for acetaminophen based on single-walled carbon nanotube-graphene nanosheet hybrid films," Sensors and Actuators B: Chemical (2012) 161(1) 648-654.

Soin, Navneet et al., "Microstructural and electrochemical properties of vertically aligned few layered graphene (FLG) nanoflakes and their application in methanol oxidation," Materials Chemistry and Physics 129(3):1051-1057, Oct. 2011.

Wen, Zhenhai et al., "Metal Nitride/Graphene Nanohybrids: General Synthesis and Multifunctional Titanium Nitride/Graphene Electrocatalyst," Advanced Materials (2011) 23, 5445-5450.

Zhao, Xin et al., "Carbon nanosheets as the electrode material in supercapacitors," Journal of Power Sources, (2009) 194(2) 1208-1212.

* cited by examiner

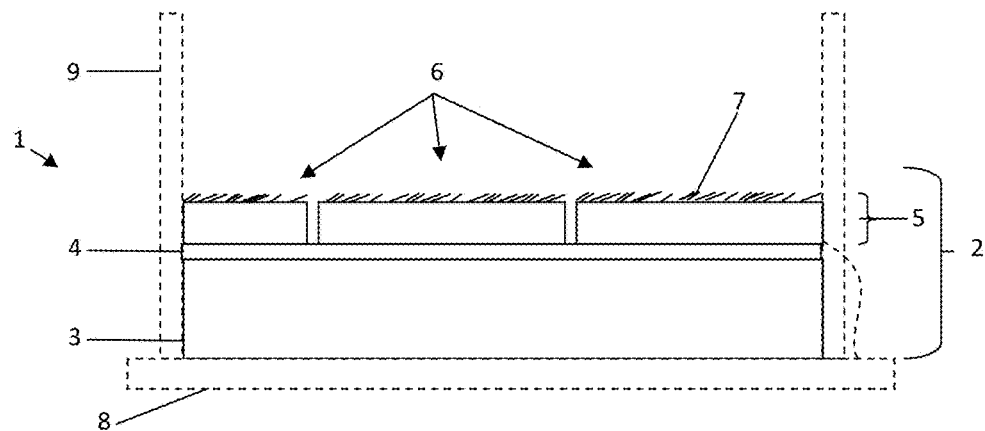
FIG. 1
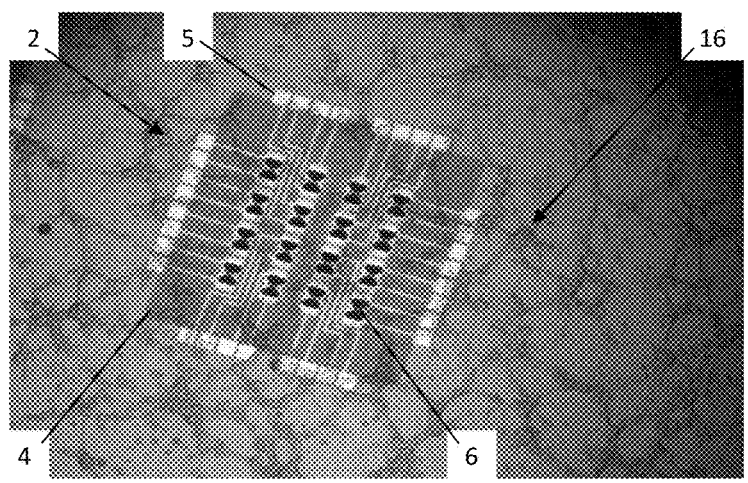
FIG. 2
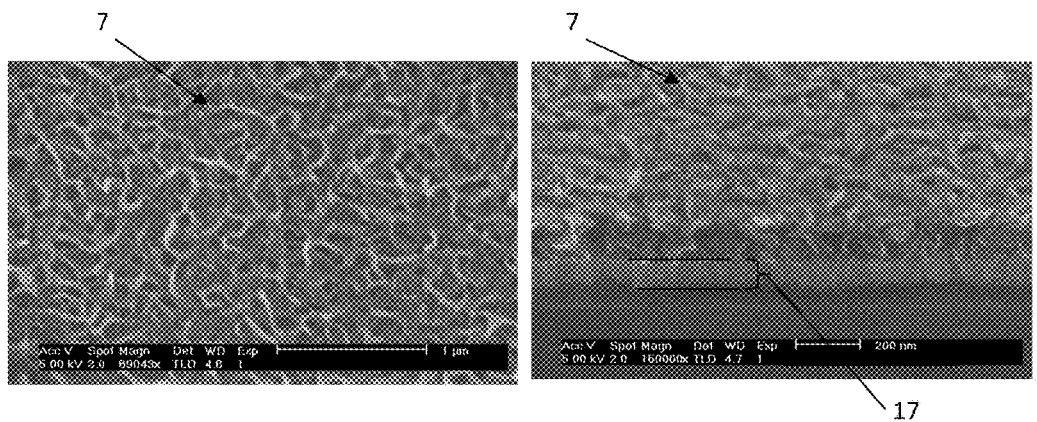
FIG. 3      FIG. 4

MICRO-STIMULATION AND DATA ACQUISITION FROM BIOLOGICAL CELLS

CROSS-REFERENCE TO RELATED APPLICATION

This application claims priority to U.S. Provisional Patent Application No. 61/658,822 filed on Jun. 12, 2012, the contents of which are hereby incorporated by reference.

FIELD OF THE INVENTION

The present invention relates to the field of biological cell stimulation and the acquisition of information from biological cells. More specifically it relates to the field of implantable micro-systems for neural information recording and neural stimulation.

BACKGROUND OF THE INVENTION

Neural recording and stimulation through micro-machined devices has been a long standing endeavour of researchers and micro-system engineers in order to improve the understanding of neural activity and to achieve purposeful modulation of neural activity, such as neuro-stimulation for the treatment of Parkinson disease, epilepsy and chronic pain. Such devices are, however, particularly challenging from both a fabrication and a signal processing point of view. One of the key components of these devices is the electrode element which interfaces the neural cells to such electronic micro-device. High charge storage capacity and low impedance are desirable properties of the electrode element for good stimulation of electro-genic cells and good data acquisition relating to the cell state, both in in vivo applications, e.g. in neural implants, and in in vitro applications, e.g. in multi-electrode array cell assays.

Platinum, titanium nitride (TiN), and metal oxides like iridium oxide ($IrO_x$) are known in the art as potential electrode materials. TiN is an especially promising material, as it advantageously combines biocompatibility and complementary metal-oxide-semiconductor (CMOS) compatibility. Furthermore, TiN offers good thermal and chemical stability. However, in order to meet the requirements for providing good stimulation and recording, highly porous TiN layers may be required to provide a sufficiently large contact area. Unfortunately, the pore resistance limits the benefits of the increased electrochemical interface area, particularly for narrow and deep pores. Moreover, TiN is less suitable for prolonged stimulation purposes as it forms a stable and insulating surface oxide.

Carbon nano-materials have also been considered as an alternative electrode material because of their good electrochemical stability as well as their high surface to volume ratio. Carbon nanotubes (CNTs) may be the most extensively studied materials of this class, and have proven to be an advantageous material choice for neural recording and stimulation devices. However, while CNTs provide good cell adhesion, their applicability may be hampered by poor adhesion between the CNTs and the substrate. Furthermore, capillary interactions between CNTs in a wet environment may reduce the effective surface area. Another disadvantage of CNTs may be that the surface density of a CNT array can lie in the range of 1% to 5% due to free space between the tubes.

For example, Scott Miserendino et al. disclose, in "Electrochemical characterization of parylene-embedded carbon nanotube nanoelectrode assays", published in Nanotechnology 17(4), a parylene-embedded carbon nano-tube nanoelectrode array in an electrochemical detector. Such array can advantageously be fabricated in a process which is compatible with standard micro-electromechanical system (MEMS) processing and which does not require additional chemical/mechanical polishing.

However, other carbon allotropes may also provide good surface to volume ratios and electrochemical stability, while being more robust than CNTs, and may thus be potentially better suited for neural recording than typical thin-film electrode materials.

SUMMARY OF THE INVENTION

It is an object of embodiments of the present invention to provide good electrochemical and physical material properties of an interface electrode in an in-vivo or in-vitro micro-device for bio-electric cell stimulation and data recording.

The above objective is accomplished by a method and device according to embodiments of the present invention.

In a first aspect, the present invention provides a semiconductor device for stimulating and/or data recording of a biological material, e.g. a complementary metal-oxide semiconductor (CMOS) device for the stimulation and recording of biological cells. The device comprises an electrode element, e.g. an electrode. This electrode element comprises: a semiconductor substrate, such as a silicon substrate, and an insulating layer, e.g. an insulating layer arranged on the semiconductor substrate. The electrode element furthermore comprises an electrode layer arranged atop the insulating layer, e.g. the electrode may comprise a conductive layer which comprises an electrode layer atop the insulating layer. The electrode layer comprises at least one electrode, in which the surface of the at least one electrode is covered by carbon nano-sheets. For example, the electrode layer may comprise a plurality of titanium nitride electrodes, where each titanium nitride electrode surface area is covered by carbon nano-sheets.

Throughout the present description, the term "nanosheets" is employed. However, this term can encompass any thin free standing graphitic films composed of individual sheet-like layers of thin graphite or multilayer graphene, such as, for example, graphene nano flakes (GNF), carbon nano flakes (CNF), carbon nano walls (CNW), carbon nanosheets (CNS), or graphene nanowalls (GNW), among others.

In a semiconductor device according to embodiments of the present invention, the at least one electrode may comprise at least one titanium nitride electrode, platinum electrode or metal oxide electrode, for example an iridium oxide $IrO_x$ electrode.

It is an advantage of embodiments of the present invention that an electrode element is provided composed of materials suitable for biomedical electrodes.

It is an advantage of embodiments of the present invention that an electrode element is provided having a high surface area to volume ratio.

It is an advantage of embodiments of the present invention that an electrode element is provided which does not require a metallic catalyst such as Ni or Co for the manufacturing process, e.g. for the carbon nano-sheet (CNS) deposition.

It is an advantage of embodiments of the present invention that a base layer may act as an effective barrier to oxidation. For example, carbon nano-sheets may advantageously be grown in a vertically oriented fashion from a graphitic base layer parallel to the underlying support, which may act as a barrier to oxidation in an aqueous environment.

It is an advantage of embodiments of the present invention that an electrode element is provided comprising an electrode material which adheres well to the substrate.

It is an advantage of embodiments of the present invention that an electrode element having a surface which is easy to functionalize. For example, the defective nature and the high proportion of exposed edge sites in carbon nano-sheet material layers may offer suitable 'active' sites for chemical sensing, fast electrochemical reactions and surface sites for further functionalization, which may be used in addition or in combination to bioelectric signal sensing in a device.

It is an advantage of embodiments of the present invention that an electrode element is provided which provides good sensitivity for recording bio-electric signals.

It is an advantage of embodiments of the present invention that an electrode element is provided which provides a high charge storage capacity and has a low impedance. For example, five times higher charge storage capacity and an almost ten times higher double layer capacitance may be achieved compared to similar titanium nitride electrodes as known in the art.

A semiconductor device according to embodiments of the present invention may also comprise integrated circuitry interconnected to the electrode element and adapted for recording and/or stimulating at least one biological cell via the electrode layer. For example, the present invention may also relate to an integrated CMOS semiconductor device for recording and stimulation of biological cells, in which this device comprises CMOS integrated circuitry and an electrode element as described hereinabove atop the CMOS integrated circuitry. This CMOS integrated circuitry may be interconnected to the electrode element and the CMOS integrated circuitry may be arranged to record and/or stimulate biological cells via the electrode element.

In a semiconductor device according to embodiments of the present invention, the electrode element may be packaged atop the integrated circuitry, e.g. atop the CMOS integrated circuitry.

In a semiconductor device according to embodiments of the present invention, the electrode element may be processed atop the integrated circuitry, e.g. directly processed atop the CMOS integrated circuitry.

In a semiconductor device according to embodiments of the present invention, the integrated circuitry may be adapted for amplification and signal processing of a signal obtained from the electrode element. For example, in some embodiments, the CMOS circuitry may comprise electronic circuitry for signal amplification and signal processing.

A semiconductor device according to embodiments of the present invention may further comprise a ring attached to the electrode element for containing a medium comprising biological material, e.g. a glass ring glued to contain biological cells in a cell medium.

A semiconductor device according to embodiments of the present invention may be an implantable device adapted for recording signals from neural tissue and/or for stimulating the neural tissue.

It is an advantage of embodiments of the present invention that a stimulation/recording device for biological cells is provided which is both biocompatible and CMOS compatible.

In a second aspect, the present invention further provides a method for fabricating a semiconductor device for stimulation and/or data recording of biological material, e.g. a semiconductor device according to the first aspect of the present invention. This method comprises providing a semiconductor substrate, e.g. a silicon substrate, which comprises a first insulating layer, providing a patterned conductive layer on top of the insulating layer and depositing and patterning a second insulating layer atop the patterned conductive layer. The patterning of the second insulation layer may be performed to create trenches to define electrode areas, e.g. to define electrodes.

The method also comprises growing carbon nano-sheets atop the second insulating layer and defining carbon nano-sheet electrode areas on the second insulating layer by etching away the carbon nano-sheets outside of the carbon nano-sheet electrode areas.

In a method according to embodiments of the present invention, providing the patterned conductive layer on top of the insulating layer may comprise providing on top of said insulating layer a patterned titanium nitride layer, a patterned platinum layer or a patterned metal oxide layer, such as a patterned iridium oxide $IrO_x$ layer.

In a method according to embodiments of the present invention, defining the carbon nano-sheet electrode areas may comprise applying a resist coating to the second insulating layer, patterning the resist coating to create carbon nano-sheets electrode areas, etching away the carbon nano-sheets outside of the carbon nano-sheet electrode areas and removing the resist coating.

For example, a method according to embodiments of the present invention may be a CMOS compatible method for fabricating a device for stimulation and/or recording of biological cells. Such method may comprise providing a silicon substrate comprising a first insulating layer, creating a conductive layer atop the insulating layer by depositing and patterning a titanium nitride layer atop the insulating layer, and depositing and patterning a second insulating layer atop the titanium nitride layer. Such method may further comprise creating carbon nano-sheet electrodes atop the insulating layer by: growing carbon nano-sheets atop the conductive layer, applying a resist coating and perform patterning to create carbon nano-sheets electrode areas, performing etching of the carbon nano-sheets outside of the carbon nano-sheet electrode areas, and stripping the resist coating. The titanium nitride layer may also be another material such as Platinum or metal oxides such as iridium oxide $IrO_x$.

In a method according to embodiments of the present invention, providing the semiconductor substrate may comprise providing a silicon dioxide material as the first insulating layer on the substrate. Additionally or alternatively, in such method, depositing and patterning the second insulating layer may comprise providing a silicon dioxide material as the second insulating layer. For example, in a method according to embodiments, the first or second insulating layer may be a silicon dioxide layer. In embodiments of the disclosure, the second insulating layer may be any material suitable for patterning trenches to define electrodes.

In a method according to embodiments of the present invention, providing the patterned titanium nitride layer may comprise depositing the titanium nitride layer by sputtering, e.g. the depositing of the titanium layer may be performed by sputtering.

In a method according to embodiments of the present invention, growing the carbon nano-sheets may comprise using a plasma process.

This plasma process may be performed using Radio Frequency Plasma-Enhanced Chemical Vapour Deposition for 1 to 5 minutes at a pressure of 0.5 Torr or lower and at a temperature in the range of 600 to 800 degrees Celsius. For example, the plasma process may be performed at low pressure, e.g. 0.5 Torr or lower, at 600 to 800 degrees Celsius using a Radio Frequency Plasma-Enhanced Chemical Vapour Deposition machine under vacuum ($1\times10^{-5}$ Torr) for 1 to 5 minutes.

This plasma process may also be performed using microwave plasma enhanced Chemical Vapour Deposition for 1 to 5 minutes at a pressure of $1\times10^{-5}$ Torr or lower and at a temperature in the range of 400 to 600 degrees Celsius. For example, the plasma process may be performed at low pressure, e.g. 0.5 Torr or lower, at 400 to 600 degrees Celsius using a microwave plasma enhanced Chemical Vapour Deposition machine under vacuum ($1\times10^{-5}$ Torr) for 1 to 5 minutes.

In a method according to embodiments of the present invention, growing the carbon nano-sheets may further comprise letting the substrate cool at a pressure of $1\times10^{-5}$ Torr or lower after applying said plasma process. For example, in some embodiments, after the step of growing carbon nano-sheets, the substrate is left to cool under vacuum ($1\times10^{-5}$ Torr).

In a method according to embodiments of the present invention, defining the carbon nano-sheet electrode areas may comprise etching away the carbon nano-sheets outside of the carbon nano-sheet electrode areas using an $O_2$ plasma. For example, the etching of the carbon nano-sheets outside of the carbon nano-sheet electrode areas may be performed using $O_2$ plasma.

A method according to embodiments of the present invention, may further comprise exposing the carbon nano-sheet electrode areas to $UV/O_3$ to increase hydrophilic behaviour of the carbon nano-sheet electrode areas. This exposing to $UV/O_3$ may comprise exposing for an exposure time in the range of less than 1 minute to 15 minutes. For example, the method may further comprise a step of increasing $UV/O_3$ exposure time of the carbon nano-sheet electrodes. This may advantageously increase the hydrophilic behaviour of the carbon nano-sheet electrodes and reduce the contact angle. In some embodiments, the $UV/O_3$ exposure time may be increased from 0 to 15 minutes.

A method according to embodiments of the present invention may further comprise characterizing the carbon nano-sheets by cyclic voltammetry and electrochemical impedance spectroscopy.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

BRIEF DESCRIPTION OF THE DRAWINGS

FIG. 1 shows an exemplary semiconductor device according to embodiments of the present invention.

FIG. 2 shows a bright field image of a multi-electrode array with patterned carbon nano-sheets electrodes according to embodiments of the present invention; hippocampal neurons from mouse are shown on top of the electrodes after 8 DIV.

FIG. 3 shows a top-view scanning electron microscopy (SEM) image of the carbon nano-sheets layer in the device according to embodiments of the present invention, which was also shown in FIG. 2, after removal of the cells with trypsin.

FIG. 4 shows a cross-sectional SEM indicating the carbon nano-sheets layer and the underlying TiN layer in the device according to embodiments of the present invention, which was also shown in FIG. 2 and FIG. 3.

Figure 5:
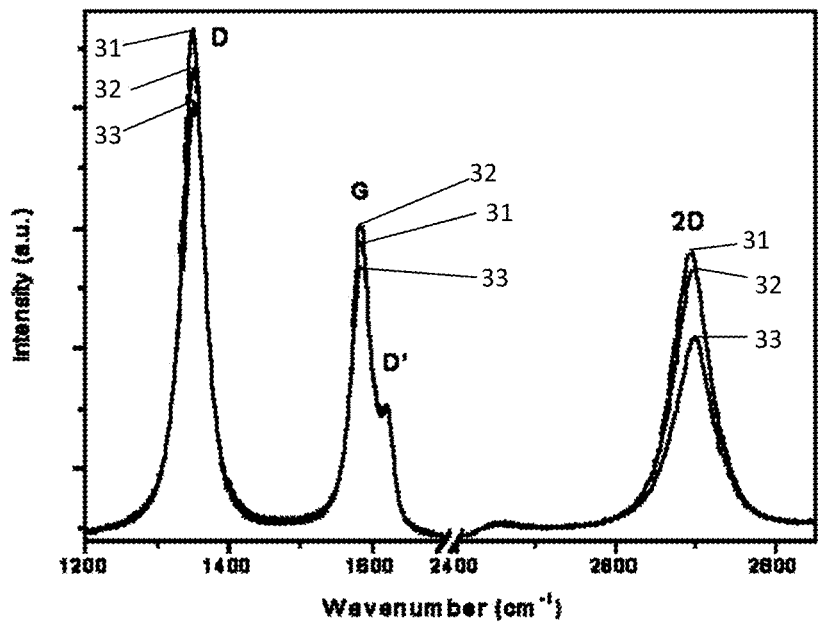
FIG. 5 shows Raman spectra ($\lambda$laser=532 nm, 0.5 mW) of a CNS layer grown on TiN in a device according to embodiments of the present invention, after 10 and 20 min exposure to $UV/O_3$.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Carbon nano-sheets as nano-structured coating materials can be deposited on top of conductive layers such as titanium nitride (TiN) electrode layers, in accordance with embodiments of the present invention, and may advantageously provide good electrochemical behaviour and biocompatibility. Carbon nano-sheets or flakes (CNS) may comprise several graphite or graphene layers stacked on top of each other, forming thin free standing graphitic films composed of individual sheet-like layers of thin graphite or multi-layer graphene. At present, there is little accepted or definite nomenclature to describe such films; however, they may be referred to as graphene nano-flakes (GNF), carbon nano-flakes (CNF) carbon nano-walls (CNW), carbon nano-sheets (CNS) or graphene nano-walls (GNW). Common to such structures is that they may be synthesized in a plasma environment. Hereinafter, the term "carbon nano-sheets" may refer to any such structures, e.g. will encompass GNF, CNW, CNS, GNW or similar films composed of individual free-standing sheet-like layers of thin graphite or multi-layer graphene. Typically these layers are considered for innovative energy storage solutions such as supercapacitors, mainly because of their high surface area to volume ratio. The latter feature also makes such structures an interesting material for biomedical electrodes. As opposed to carbon nanotubes (CNTs), no metallic catalysts like Ni or Co are required for CNS deposition, and CNS adheres very well to the substrate. Furthermore, the ease of CNS surface functionalization is an additional benefit. Nevertheless, CNS may not have been previously used for neural recording or stimulation electrodes.

In a first aspect, the present invention relates to a semiconductor device for stimulating and/or data recording of a biological material. This semiconductor device comprises an electrode element which comprises a semiconductor substrate, an insulating layer arranged on the semiconductor substrate, and an electrode layer arranged atop the insulating layer. The electrode layer comprises at least one electrode, in which the surface of the at least one electrode is covered by carbon nano-sheets.

Referring to FIG. 1, an exemplary semiconductor device 1 according to embodiments of the present invention is shown. This semiconductor device for stimulating and/or data recording of a biological material may be a biocompatible semiconductor device.

The semiconductor device comprises an electrode element 2, which comprises a semiconductor substrate 3, e.g. a silicon (Si) substrate, and an insulating layer 4 arranged on the semiconductor substrate. For example, the insulating layer 4 may be an oxide or nitride layer, such as a silicon dioxide $SiO_2$ layer.

The device further comprises an electrode layer 5 arranged atop the insulating layer 4. This electrode layer 5 comprises at least one electrode 6. The at least one electrode 6 may comprise at least one titanium nitride electrode, platinum electrode, or metal oxide electrode. For example, the electrode layer 5 may comprise a conducting layer, e.g. comprising titanium nitride TiN material, platinum material, or a metal oxide electrode material. The electrode layer 5 may also comprise a second insulating layer, e.g. comprising an insulating oxide or nitride material, such as a silicon dioxide $SiO_2$, for example arranged to partially cover the conducting layer. The electrode layer may be adapted in composition and structure to be compatible with carbon nano-sheet (CNS) processing, e.g. the electrode layer 5 may be compatible in the sense that CNS can be grown on this conductive layer. The at least one electrode 6 may be defined, e.g. delineated, in the electrode layer 5 by micro-patterning of the conducting layer and the second insulating layer, e.g. manufactured by etching of these layers. The surface of the at least one electrode 6 is furthermore covered by carbon nano-sheets 7. For example, the electrode layer 5 may comprise at least one titanium nitride TiN electrode, a second insulating layer, e.g. a $SiO_2$ layer, and a carbon nano-sheet layer, e.g. carbon nano-sheets grown on the titanium nitride electrode material.

The semiconductor device 1 may further comprise integrated circuitry 8 interconnected to the electrode element 2 and adapted for recording and/or stimulating at least one biological cell via the electrode layer 5, as schematically shown in FIG. 1. The electrode element 2 may be packaged atop the integrated circuitry 8, or the electrode element 2 may be processed atop the integrated circuitry 8, e.g. the substrate 3 may also have the integrated circuitry provided thereon. The integrated circuitry 8 may be adapted for amplification and signal processing of a signal obtained from the electrode element 2, e.g. according to methods of bioelectric signal processing as known in the art.

Furthermore, a semiconductor device 1 according to embodiments of the present invention may comprise a plurality of electrode elements 2, e.g. in a multi-site stimulation and/or recording implant or a multi-well bioelectrical signal analysis device.

The semiconductor device 1 may further comprise a ring 9, e.g. a glass ring, attached to the electrode element 2, e.g. glued to the electrode element 2, such as e.g. to an outer surface thereof, for containing a medium comprising biological material, for example for forming a sample well in a in vitro bioelectric signal analysis system. Therefore, in some embodiments, study of in vitro cultures can be achieved. For example, in such embodiments, at least one multi-electrode test chip, e.g. an electrode element 2, may be packaged on a custom printed circuit board (PCB). A glass ring may furthermore be glued on top of the PCB to contain the cells and the cell medium. The PCB may also contain custom electronic circuits for signal amplification and signal processing.

However, the present invention also relates to an implantable device comprising a semiconductor device 1 according to embodiments of the present invention, in which the implantable device is adapted for recording signals from neural tissue and/or for stimulating said neural tissue.

CNS-coated TiN electrodes according to embodiments adhere well to neural tissue, as is demonstrated by following in vitro example, in which cultured hippocampal neurons on patterned CNS samples are shown. FIG. 2, FIG. 3 and FIG. 4 show exemplary bright field, top-down and cross-section scanning electron microscopy (SEM) images of patterned TiN electrodes coated with carbon nano-sheets according to embodiments of the present invention. These electrodes are furthermore covered with neuron cells 16. It can be seen that the specific nano-structure of the CNS layer is clearly distinguishable. In this example, the sheets 7 consist of vertically aligned graphene layers with a total thickness in the range of 200-300 nm. In a device according to embodiments of the present invention, the thickness range may be in the range of 150 nm to 2 µm. The carbon nano-sheets 7 are, in this example, provided onto a patterned TiN conductive layer 17.

Atomic Force Microscopy (AFM) analysis on blanket substrates revealed an average surface roughness $R_a$ of 21.9 nm and a root mean square roughness RMS of 27.1 nm, while the starting TiN layers have a $R_a$=0.9 nm and RMS=1.1 nm. These measurements were done using a Nanoscope IVa Dimension 3100 (tapping mode).

The Raman spectral data is shown in FIG. 5, on which the peaks are indicated for the spectrum of an as-grown CNS layer 31, a CNS layer after 10 minutes of $UV/O_3$ treatment 32, and a CNS layer after 20 minutes of $UV/O_3$ treatment 33, as described further hereinbelow.

In a second aspect, the present invention relates to a method for fabricating a semiconductor device for stimulation and/or data recording of biological material, e.g. a semiconductor device according to embodiments of the first aspect of the present invention. For example, such method may be a method to fabricate CNS-coated TiN electrodes for in vivo or in vitro applications. A dedicated process flow may allow patterning carbon nano-sheets with diameters down to a few micrometers.

Figure 6:
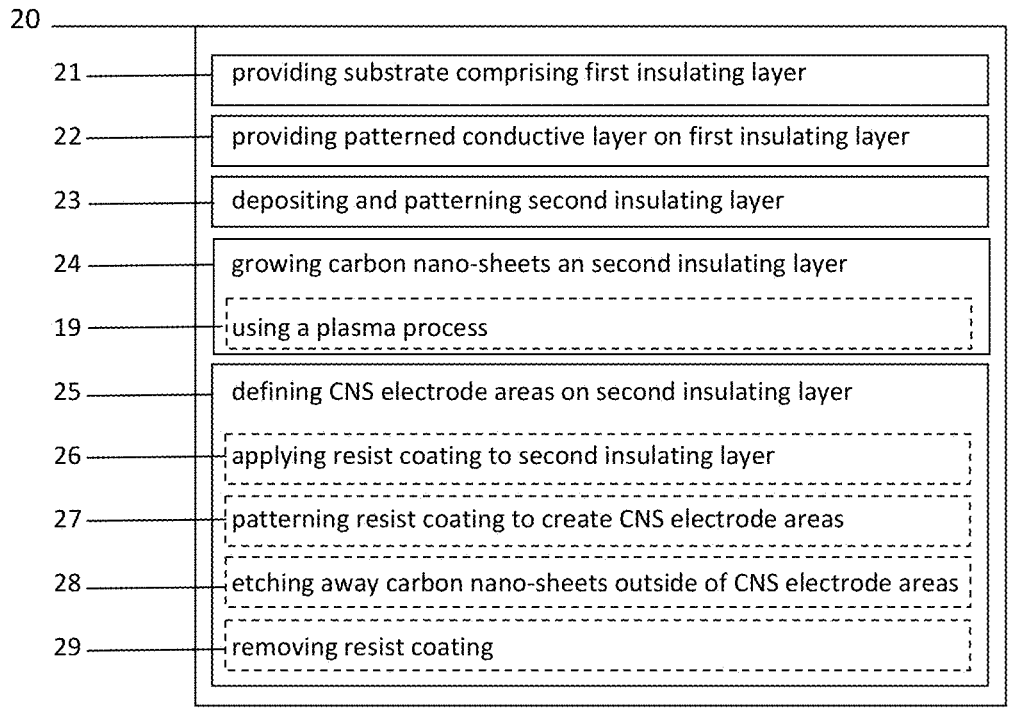
FIG. 6 illustrates a method according to embodiments of the present invention.

FIG. 6 shows an exemplary method 20 according to embodiments of the present invention. The method 20 comprises providing 21 a semiconductor substrate comprising a first insulating layer, providing 22 a patterned conductive layer on top of the first insulating layer and depositing, and patterning 23 a second insulating layer atop the patterned conductive layer.

For example, providing 21 the semiconductor substrate may comprise providing a silicon dioxide material as the first insulating layer on the substrate, and/or depositing 23 and patterning the second insulating layer may comprise providing a silicon dioxide material as the second insulating layer. Providing 22 the patterned conductive layer on top of the insulating layer may comprise providing on top of the first insulating layer a patterned titanium nitride layer, a patterned platinum layer or a patterned metal oxide layer. For example, a patterned titanium nitride layer may be provided by depositing the titanium nitride layer in a sputtering process.

The method 20 further comprises growing 24 carbon nano-sheets atop the second insulating layer. Growing 24 the carbon nano-sheets may comprise using 19 a plasma process. This plasma process may be performed using Radio Frequency Plasma-Enhanced Chemical Vapour Deposition for 1 to 5 minutes at low pressure, e.g. at a pressure of 0.5 Torr or lower, and at a temperature in the range of 600 to 800 degrees Celsius. Alternatively, the plasma process may be performed using microwave plasma enhanced Chemical Vapour Deposition for 1 to 5 minutes in vacuum, e.g. at a pressure of $1\times10^{-5}$ Torr or lower, and at a temperature in the range of 400 to 600 degrees Celsius.

Furthermore, growing 24 the carbon nano-sheets may further comprise letting the substrate cool in vacuum, e.g. at a pressure of $1\times10^{-5}$ Torr or lower, after applying such plasma process.

The method 20 also comprises defining 25 carbon nano-sheet electrode areas on the second insulating layer by etching away the carbon nano-sheets outside of the carbon nano-sheet electrode areas, e.g. using an $O_2$ plasma. For example, in embodiments of the present invention, defining 25 the carbon nano-sheet electrode areas may comprise applying 26 a resist coating to the second insulating layer, patterning 27 the resist coating to create the carbon nano-sheet electrode areas, etching 28 away the carbon nano-sheets outside of the carbon nano-sheet electrode areas, and removing 29 the resist coating.

Furthermore, the method 20 may comprise exposing the carbon nano-sheet electrode areas to $UV/O_3$ to increase hydrophilic behaviour of the carbon nano-sheet electrode areas, e.g. exposing for an exposure time in the range of less than 1 minute to 15 minutes.

For example, Raman spectral data is shown in FIG. 5, on which the peaks are indicated for the spectrum of an as-grown CNS layer 31, a CNS layer after 10 minutes of $UV/O_3$ treatment 32, and a CNS layer after 20 minutes of $UV/O_3$ treatment 33. In this example, CNS layers were grown on a TiN electrode base layer. CNS layers can be described by three Raman bands common to graphitic ($sp^2$ bonded) carbon (nano) structured materials, e.g. D (1348 $cm^{-1}$), G (1584 $cm^{-1}$) and 2D (~2694 $cm^{-1}$). In this example, also D'(1620 $cm^{-1}$) may be observed. The peak maxima listed hereinabove in parenthesis are those recorded from a 532 nm green laser excitation. The D-peak may be the most intense peak recorded, e.g. due to the high portion of graphite edge sites exposed and the short distance (~10 nm) between adjacent defects. In fact, the as-grown CNS layers may have edges exposed as thin as three graphene layers. Peak intensity ratios, as outlined in the table hereinbelow, may be a measure of structural order and defect densities. $UV/O_3$ treatment on CNS layers, as described further below in relation to fabrication methods according to embodiments of the second aspect of the present invention, can play a twofold role: the sheets can be etched whilst defective C—H sites can be chemically modified to form oxygen terminated species. Table 1 hereinbelow outlines intensity ratios $I_D/I_G$, $I_G/I_{2D}$ and 2D band peak position. A slight reduction in the $I_D/I_G$ ratio after 10 min may indicate a removal of any amorphous (sp) species that may absorb on the sheets during a plasma growth process or from a TiN—CNS interface layer. By increasing the $O_3$ exposure, the $I_D/I_G$ ratio may rise. However, defects and oxygen functionalities may increase whilst a portion of the carbon layer is removed as peak intensities are reduced indicating a loss of material. An increase of the $I_G/I_{2D}$ and 2D peak upshift may be indicative of etching of the sheets as an individual CNS is thicker (more graphene layers) closer to the growth substrate. Hence, as the overall layer height is reduced through preferential etching at the edges the average width of the shortened sheets, e.g. the number of graphene layers standing perpendicular to the TiN surface, may increase.

TABLE 1

|  | $I_D/I_G$ | $I_G/I_{2D}$ | 2D-pos($cm^{-1}$) |
| --- | --- | --- | --- |
| Reference | 1.61 | 1.04 | 2694 |
| 10 min UV/O3 | 1.42 | 1.14 | 2697 |
| 20 min UV/O3 | 1.50 | 1.28 | 2699 |

Figure 7:
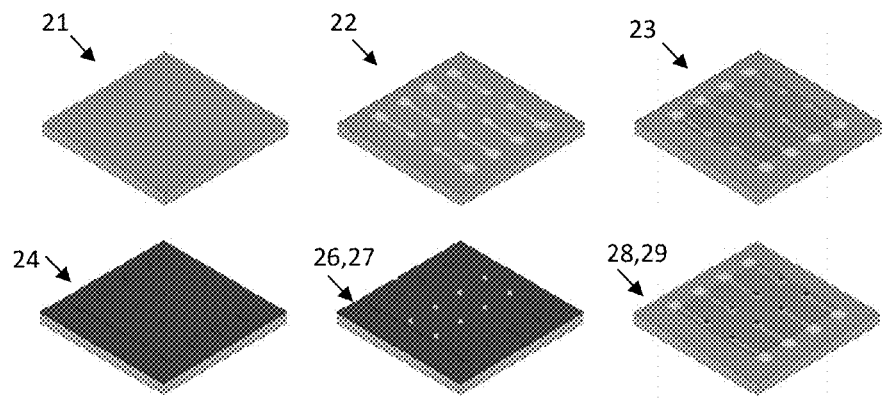
FIG. 7 shows a schematic presentation of a fabrication process for carbon micro-electrodes according to embodiments of the present invention.

FIG. 7 shows the steps of an exemplary manufacturing method according to embodiments of the present invention. In particular, FIG. 7 schematically describes the fabrication process of an array with individually addressable electrodes and electrode diameters down to 25 μm. In some embodiments, electrode diameters can vary from 1 μm to 500 μm. However, embodiments of the present invention are not necessarily restricted to this range. The top row of images in FIG. 7 illustrates, from left to right, the intermediate results of: providing 21 a semiconductor substrate comprising a first insulating layer, providing 22 a patterned conductive layer on top of the first insulating layer and depositing, and patterning 23 a second insulating layer atop the patterned conductive layer.

In this example, providing 21 a semiconductor substrate with a first insulating layer comprises $SiO_2$ deposition on the substrate. The underlying films may for example comprise or consist of a 200 nm thermal $SiO_2$ layer grown on a 4 inch Si substrate, but larger or smaller wafer sizes can also be employed in embodiments of the present invention. In embodiments of the present invention, the thickness of the $SiO_2$ can vary from a few μm (e.g. 5 μm) to 50 nm but is not necessarily restricted to this range.

Providing 22 the patterned conductive layer on top of the first insulating layer may comprise TiN lift-off patterning. In the example illustrated in FIG. 7, a 70 nm TiN layer was sputtered from a Ti target in a $N_2$ atmosphere and patterned using lift-off. In embodiments of the present invention, the thickness of the TiN layer can vary from 10 nm to 500 nm, but is not necessarily restricted to this range.

The step of depositing and patterning 23 a second insulating layer atop the patterned conductive layer may comprise $SiO_2$ deposition and patterning. In the example shown in FIG. 7, a 200 nm $SiO_2$ layer was deposited on top of the TiN layer. After resist coating and exposure the oxide layer was etched in buffered HF to define oxide trenches on top of the TiN, e.g. this layer was removed on top of the electrode areas and the bond pads by standard lithography and etch processes. If appropriately timed, this step may advantageously help cleaning the TiN surface prior to the CNS deposition.

The bottom row of FIG. 7 shows, from left to right, the result of the consecutive steps of: growing 24 carbon nano-sheets on the second insulating layer, e.g. of CNS deposition on the $SiO_2$ layer; applying 26 a resist coating and patterning 27; and etching 28 away the carbon nano-sheets outside of the carbon nano-sheet electrode areas and stripping 29 the resist coating.

Growing 24 carbon nano-sheets on the second insulating layer may comprise growing carbon layers in at low pressure (e.g. 0.5 Torr) 13.56 MHz RF generator, for example using an Oxford Instruments plasma technology UK. NANOCVD, as was used for the example illustrated in FIG. 7. In a typical CNS growth application, the wafer may be allowed to reach a heater temperature of 750° C. A suitable range of temperature may be 600 to 800° C. in an RF PECVD system and 400 C to 600° C. in a microwave plasma enhanced (MPE) CVD under vacuum (e.g. $1 \times 10^{-5}$ Torr) for 1 minute, so as to reach thermal equilibrium.

In some embodiments, the deposition time may range up to 5 minutes. Thermal equilibrium can be established in the pre-treatment step as well. To prepare the wafer surface, an $H_2$ plasma pre-treatment (300 W) may be carried out, e.g. for 15 minutes. Pre-treating for 15 minutes may for example be sufficient to ensure thermal equilibrium. A typical range for pre-treatment may be 1 to 15 minutes, e.g. at 0.5 Torr, however, if treatment conditions and equipment are suitable for lower pressures, it may be advantageous to lower the pressure to, for example, 0.05 Torr.

To deposit the carbon nano-sheets, $CH_4$ (50 sccm) may be flown into the plasma chamber in a $CH_4/H_2$ ratio of 1:2, or $C_2H_2$ (10 sccm) may be used in a $C_2H_2/H_2$ ratio of 1:10 for a 300 W plasma. Although other reaction gases may be suitable, and other gas ratios may be used in accordance with embodiments of the present invention, the gases and gas ratios mentioned hereinabove advantageously produce few layers per sheet and a high surface density, without forming a dense amorphous carbon film when applying a total pressure of 0.5 Torr. In some embodiments, a higher powered plasma treatment can be selected, such as 900 W. A high RF power, e.g. 300 W, and a low total pressure may preferably be selected in embodiments of the present invention to produce atomic hydrogen and to achieve a low deposition rate.

In the example illustrated in FIG. 7, the substrate was removed from the chamber and allowed to cool under vacuum ($1 \times 10^{-4}$ Torr) for 5 minutes. After the carbon nano-sheet growth, a second patterning step was carried out to locally protect the CNS electrode areas, while the rest of the CNS were etched using an $O_2$ plasma. Thus, the second patterning step may be performed to define the CNS electrode areas and leave the bond pads free of CNS.

The smallest electrode diameters obtained in the present example are 25 µm; however, the fabrication process according to embodiments may be suitable for fabricating even smaller electrodes with diameters down to a few microns. In embodiments of the present invention, electrode diameters can vary from 1 µm to 500 µm, although the present invention is not necessarily restricted to this range.

The carbon nano-sheets, grown on TiN, have been characterized by cyclic voltammetry (CV) and electrochemical impedance spectroscopy (EIS), which are commonly used techniques to characterize electrode materials. $UV/O_3$ treatment provides a way to improve the electrochemical behaviour of the manufactured electrode elements by firstly increasing the wettability through polarity change and secondly by introducing redox couples and additional surface charge. For example, a five-fold improvement in impedance was obtained using CNS coated electrodes over reference TiN electrodes, which were fabricated with the steps in the process shown in FIG. 7 up to oxide opening, e.g. by performing steps 21, 22, and 23.

In this example, biocompatibility was checked by culturing hippocampal neurons from mice. After 8 days in vitro, the neurons formed stable networks and the samples were used for in vitro recording of the action potentials. Neural spikes were recorded with a signal-to-noise ratio (SNR) as high as 6.4. This may be a factor of 5 improvement compared to standard TiN electrodes as known in the art under the same conditions.

Figure 8:
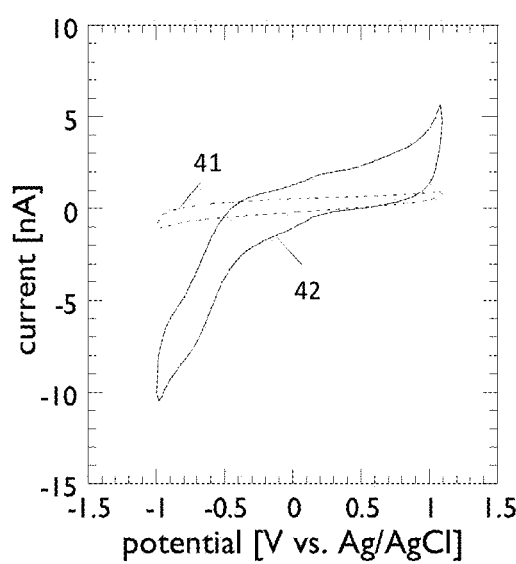
FIG. 8 shows cyclic voltammograms of a reference TiN electrode as known in the art and a CNS electrode according to embodiments of the present invention in PBS at a scan rate of 0.5V/s.
Figure 9:
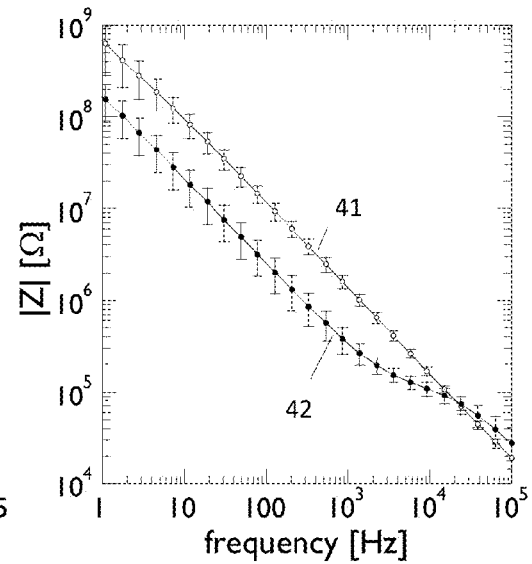
FIG. 9 shows a plot of the impedance spectra comparing TiN electrodes as known in the art to the CNS electrodes according to embodiments of the present invention. At 1 kHz, the impedance of the 25 μm carbon nano-sheets micro-electrode is 400 kΩ which is about 5 times lower than that of the TiN reference microelectrode.

The scaled carbon nano-sheets electrodes were characterized using cyclic voltammetry (CV) and electrochemical impedance spectroscopy (EIS) in a standard electrochemical three-electrode cell with a Pt reference electrode and an Ag/AgCl counter electrode. The measurements were performed in phosphate buffered saline (PBS, 20 mM, 150 mM NaCl) with a pH=7.4. The potential of the working electrode was swept between −1.0 and 1.1 V at a scan rate of 0.5V/s. A comparison between the TiN electrode 41 and the carbon nano-sheets coated TiN electrode 42 produced by the exemplary method shown in FIG. 7, having a diameter Ø=25 µm, are illustrated in FIG. 8. The calculated cathodal charge storage capacity ($CSC_c$), which is important for efficient stimulation of cells, was found to be $1.31 \pm 0.07$ mC/cm² in the case of the carbon nano-sheets and $0.27 \pm 0.05$ mC/cm² for the TiN electrodes. The corresponding impedance measurements are illustrated in FIG. 9.

The double layer capacitance, slope n and spreading resistance were extracted using a model where a constant phase angle element is put in series with a resistance $R_s$. The constant phase angle element accounts for the capacitive behaviour of the electrode while $R_s$ represents the spreading resistance at higher frequencies. The results for different electrode materials are compared in the table hereinbelow. Similar to TiN, the electrodes coated with carbon nano-sheets exhibit a capacitive behaviour with a slope n close to 0.9. Table 2 shows the extracted parameters from the impedance spectra comparing TiN and CNS electrodes, in which $R_S$ represents the spreading resistance at higher frequencies, n the slope of the capacitance dominated impedance behaviour and $C_{dl}$ the extracted double layer capacitance.

TABLE 2

| Electrode material | Diameter [µm] | $R_s$ [kΩ] | n | $C_{dl}$ [pF] |
|---|---|---|---|---|
| TiN | 25 | — | 0.88 ± 0.02 | 17 ± 4 |
| CNS | 25 | 50 ± 13 | 0.89 ± 0.01 | 82 ± 22 |
| CNS + 15 min UV/O3 | 25 | 69 ± 6 | 0.90 ± 0.01 | 136 ± 29 |
| TiN | 50 | 37 ± 7 | 0.89 ± 0.01 | 103 ± 21 |
| CNS | 50 | 32 ± 4 | 0.89 ± 0.01 | 163 ± 23 |
| CNS + 15 min UV/O3 | 50 | 39 ± 3 | 0.93 ± 0.01 | 1193 ± 185 |

Figure 12:
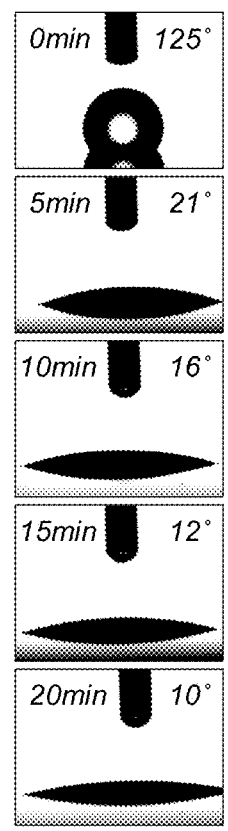
FIG. 12 shows the contact angles, as measured on blanket CNS layers, for different $UV/O_3$ treatments in a method according to embodiments of the present invention.

As is the case for CNTs, the carbon nano-sheets without additional $UV/O_3$ may be found to be very hydrophobic. Contact angle measurements revealed an angle of 125°, as shown in FIG. 12. However, $UV/O_3$ treatment can be used as a means to reduce the contact angle in accordance with embodiments of the present invention, and thus may offer the advantage of improving the hydrophilic behaviour of the CNS electrode elements.

Figure 10:
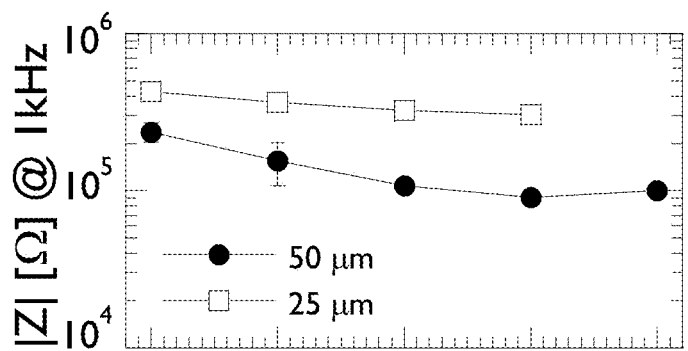
FIG. 10 shows the impedance |Z| at f=1 kHz as function of the $UV/O_3$ exposure time given prior to electrochemical measurements, relating to a method according to embodiments of the present invention.
Figure 11:
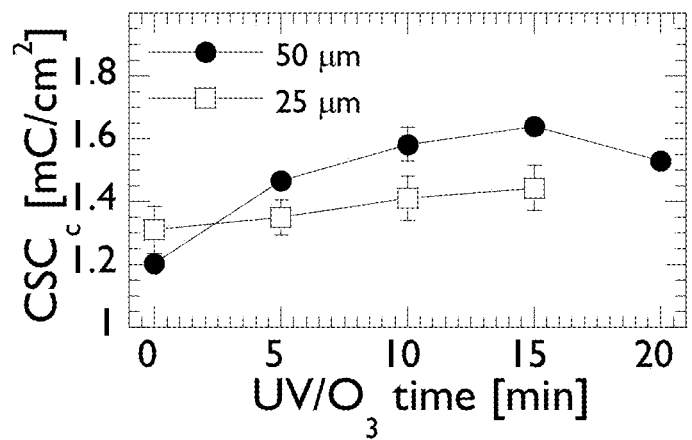
FIG. 11 shows the extracted CSCc at 0.5V/s scan rate as function of the $UV/O_3$ exposure time, relating to a method according to embodiments of the present invention.

The $UV/O_3$ exposure time may be increased from 0 to 15 minutes. As an advantage, impedance and $CSC_c$ can be improved. FIG. 10 and FIG. 11 illustrate respectively the behaviour of $CSC_c$, and the extracted impedance at 1 kHz as a function of the $UV/O_3$ time. With increasing $UV/O_3$ exposure time, both the impedance and $CSC_c$ may improve, e.g. up to good values of impedance and $CSC_c$ for electrode applications occurring around 15 minutes.

The improvement at lower exposure times may be explained by the changing surface wettability from hydrophobic (contact angle of 125°) to hydrophilic (contact angle of) ~10° due to an increase in the amount of carbon-oxygen bonds. The CNS/electrolyte interfacial contact and reaction may thus be enhanced. In the present example of embodiments of the present invention, extending the exposure time beyond 15 minutes did not show a significant further improvement of the wettability, although other exposure times may be appropriate in different choices of materials or treatment, as will be understood by the person skilled in the art.

Figure 13:
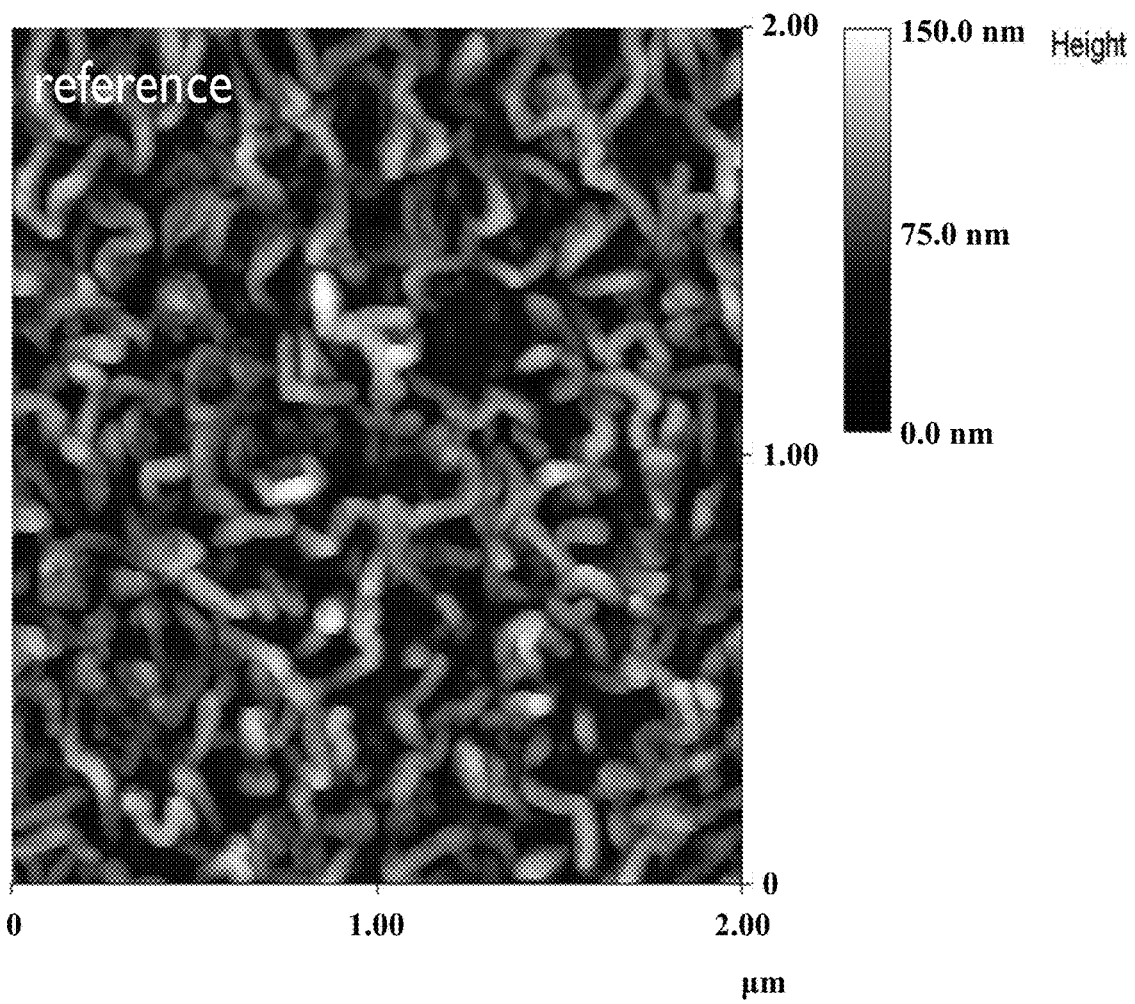
FIG. 13 shows a top-view AFM scan of carbon nano-sheets after growth according to embodiments of the present invention.
Figure 14:
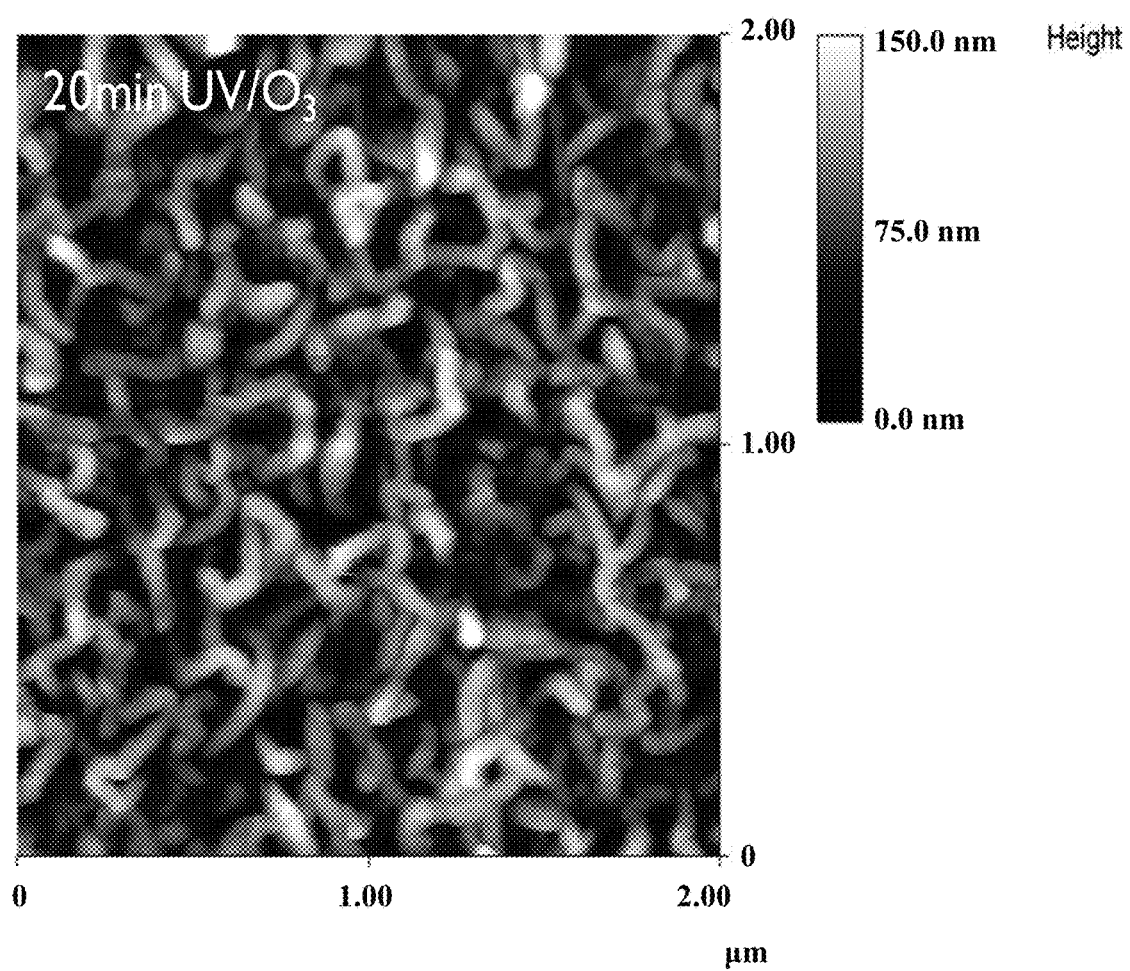
FIG. 14 shows a top-view AFM scan of carbon nano-sheets after exposure to a 20 min $UV/O_3$ treatment according to embodiments of the present invention.

Moreover, FIG. 10 and FIG. 11 may demonstrate that the performance of the electrode can be degraded by longer exposure times. This may be attributed to the possible lateral and vertical etching of the CNS, which may reduce the size of the electrodes and height of the layers. This was confirmed by SEM, which showed that the height is reduced compared to the as deposited sample. AFM analysis of the CNS layers after 20 min $UV/O_3$, shown in FIG. 14, showed an increase in roughness compared to the reference sample which was not $UV/O_3$ treated, shown in FIG. 13. This may indicate that there is a trade-off between increased wettability and the physical etching and/or other damage effects on the layers by $UV/O_3$ treatment. This may be in line with the reduced impact of the $UV/O_3$ treatment observed for the smaller electrodes, where the lateral etching of the electrode becomes more critical.

Before culturing cells on the samples in this illustrative example, the sample was exposed to 15 min UV/$O_3$. Hippocampal neurons were isolated from E18 FVB strain mice according to established procedures. Timed pregnant mice were euthanized, and embryos were isolated. Hippocampi were dissected from both hemispheres in sterile Hanks' buffered saline solution (HBSS) and incubated in 0.25% trypsin for 15 min in an incubator at 37° C. and 5% $CO_2$ atmosphere. After trypsinization, cells were washed three times with HBSS and mechanically dissociated. The cells originating from half of the hippocampus were seeded on the chips in a MEM medium supplemented with 10% horse serum. After 4 hours, the medium was replaced with a neurobasal medium containing 2% B27 supplement and 0.125% glutamate.

Figure 15:
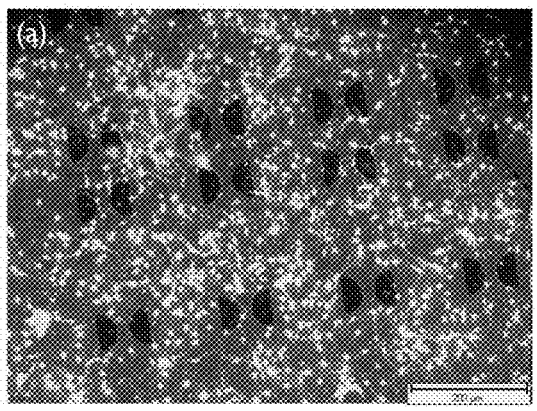
FIG. 15 shows a picture of calcein-labeled hippocampal neurons from E18 FVB strain mice on CNS electrodes according to embodiments of the present invention after 8 days in vitro, at a magnification of 5×.
Figure 16:
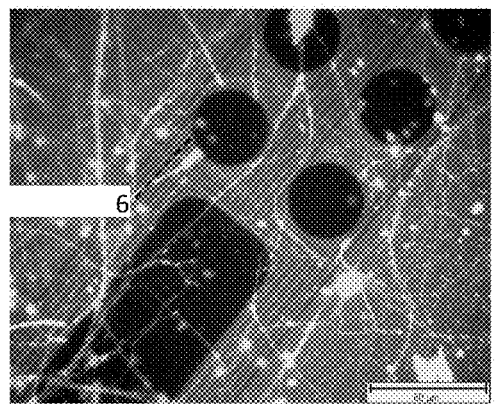
FIG. 16 shows a picture of calcein-labeled hippocampal neurons from E18 FVB strain mice on CNS electrodes according to embodiments of the present invention after 8 days in vitro, at a magnification of 20×.

In FIG. 15 and FIG. 16, pictures of calcein-labeled hippocampal neurons on patterned CNS electrodes are shown after 8 days of culturing. Stable networks can be observed both on the oxide areas and the CNS areas, indicating that there may be no issue in biocompatibility of the material. Similar samples as shown in FIG. 16 have been used for the in vitro recordings.

The in vitro example setup consisted of a mechanical device to hold and allow electrical contact to the multi-electrode test chips and a PCB containing custom electronic circuits for signal amplification and processing. All the recordings were performed with a gain of 1000 V/V and a band-pass filter from 300 Hz to 6 kHz, in order to properly isolate spontaneous action potentials in the cells. Processed signals were sampled at 20 kHz and digitized (12 bits). The interface with the computer was done through a National Instruments USB-6259 data acquisition card. Custom-developed acquisition software in Matlab® (MathWorks, Inc.) allows the programming of the electronic circuits as well as the real-time transmission, display and storing of the recorded data. Wave_Clus was used to perform clustering of spontaneous action potentials recorded on CNS and TiN electrodes. Wave_Clus is a Matlab® toolbox that performs thresholding and sorting of spikes. In this way, spikes with similar shape, e.g. which could eventually originate from a same neuron or a same unit, may be separated, e.g. sufficiently different spikes, e.g. corresponding to different units, may be sorted into different clusters.

Figure 17:
FIG. 17 shows an in vitro extracellular recording of action potentials from hippocampal neurons cultured on top of TiN electrodes as known in the art with 50 μm diameter.
Figure 19:
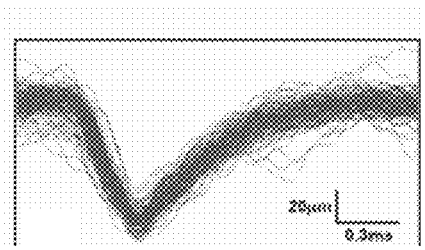
FIG. 19 shows time-aligned raw neural spikes extracted from the dataset shown in FIG. 17.
Figure 18:
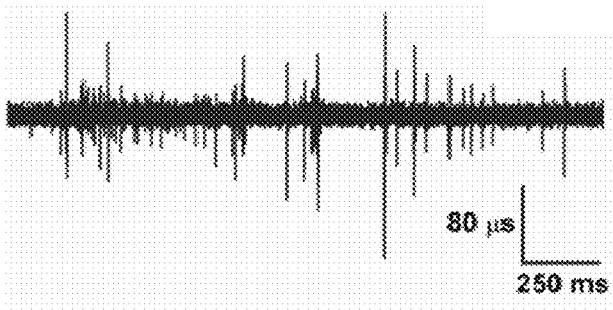
FIG. 18 shows an in vitro extracellular recording of action potentials from hippocampal neurons cultured on top of CNS according to embodiments with 50 μm diameter.
Figure 20:
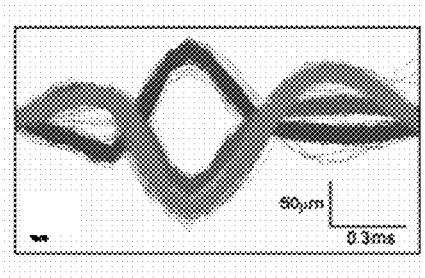
FIG. 20 shows time-aligned raw neural spikes extracted from the dataset shown in FIG. 18.

Recorded signals were amplified with a gain of 1000 V/V and band-pass filtered between 300 and 6 kHz. Spike sorting algorithms were applied to the datasets. The recorded action potentials are shown in FIG. 17, for the TiN electrode and in FIG. 18 for the CNS electrode. The time-aligned raw neural spikes extracted from the dataset of the TiN electrode can be found in FIG. 19. One cluster was detected with 148 spikes and a signal-to-noise ratio of 2.5. Time-aligned raw neural spikes extracted from the CNS dataset are shown in FIG. 20. In this case, three different clusters were detected with 253, 238 and 204 spikes, respectively, and signal-to-noise ratios of 4.3, 4.1 and 6.4, respectively.

We claim:

1. A semiconductor device for stimulating and/or data recording of a biological material, the semiconductor device comprising:
an electrode element which comprises:
a semiconductor substrate;
an electrode layer that comprises at least one electrode, the electrode layer further comprising:
a conducting layer; and
one or more carbon nano-sheets that are supported by the conducting layer such that a test medium comprising biological material can be placed in direct contact with the one or more carbon nano-sheets; and
an insulating layer arranged between the semiconductor substrate and the electrode layer; and
integrated circuitry that is complementary metal oxide semiconductor (CMOS) compatible and biocompatible, and is connected to the electrode element and adapted for at least one of recording or stimulating at least one biological cell in vitro via the electrode layer.

2. The semiconductor device according to claim 1, wherein the electrode element is at least one of packaged atop the integrated circuitry or processed atop the integrated circuitry.

3. The semiconductor device according to claim 1, wherein the integrated circuitry comprises a complementary metal oxide semiconductor (CMOS) device or a printed circuit board (PCB), the integrated circuitry being further adapted for amplification and signal processing of a signal obtained from the electrode element.

4. The semiconductor device according to claim 1, further comprising a ring configured for containing the test medium comprising the biological material, wherein the ring is attached to the electrode element.

5. The semiconductor device according to claim 1, wherein the semiconductor device is an implantable device adapted for at least one of recording signals from neural tissue or stimulating the neural tissue.

6. The semiconductor device of claim 1, wherein the electrode layer is formed on the insulating layer.

7. A biosensing system comprising a semiconductor device, wherein the semiconductor device comprises:
an electrode element which comprises:
a semiconductor substrate;
an electrode layer that comprises at least one electrode, the electrode layer further comprising:
a conducting layer; and
one or more carbon nano-sheets that are supported by the conducting layer such that a test medium comprising biological material can be placed in direct contact with the one or more carbon nano-sheets; and
an insulating layer arranged between the semiconductor substrate and the electrode layer; and
integrated circuitry that is complementary metal oxide semiconductor (CMOS) compatible and biocompatible, and is connected to the electrode element and adapted for at least one of recording or stimulating at least one biological cell in vitro via the electrode layer.

8. The semiconductor device of claim 1, wherein the conducting layer comprises titanium nitride (TiN), platinum, or a metal oxide.

9. The semiconductor device of claim 1, wherein the insulating layer contacts the electrode layer and the semiconductor substrate.

10. The biosensing system of claim 7, wherein the conducting layer comprises titanium nitride (TiN), platinum, or a metal oxide.

11. The biosensing system of claim 7, wherein the insulating layer contacts the electrode layer and the semiconductor substrate.

12. The biosensing system of claim 7, wherein the electrode element is at least one of packaged atop the integrated circuitry or processed atop the integrated circuitry.

13. The biosensing system of claim 7, wherein the integrated circuitry comprises a complementary metal oxide semiconductor (CMOS) device or a printed circuit board (PCB), the integrated circuitry being further adapted for amplification and signal processing of a signal obtained from the electrode element.

14. The biosensing system of claim 7, further comprising a ring configured for containing the test medium comprising the biological material, wherein the ring is attached to the electrode element.

15. The biosensing system of claim 7, wherein the semiconductor device is an implantable device adapted for at least one of recording signals from neural tissue or stimulating the neural tissue.

16. The biosensing system of claim 7, wherein the electrode layer is formed on the insulating layer.

* * * * *